(12) United States Patent
Yousef et al.

(10) Patent No.: US 9,128,048 B2
(45) Date of Patent: Sep. 8, 2015

(54) METHOD FOR ONLINE DETERMINATION OF CURE STATUS OF GLASS FIBER PRODUCTS

(75) Inventors: Samer T. Yousef, Granville, OH (US); Michael D. Pietro, New Albany, OH (US); Wei Li, New Albany, OH (US); Elaina M. Carpino, Hebron, OH (US)

(73) Assignee: Owens Corning Intellectual Capital, LLC, Toledo, OH (US)

( * ) Notice: Subject to any disclaimer, the term of this patent is extended or adjusted under 35 U.S.C. 154(b) by 434 days.

(21) Appl. No.: 13/089,457

(22) Filed: Apr. 19, 2011

(65) Prior Publication Data

US 2012/0268586 A1    Oct. 25, 2012

(51) Int. Cl.
*H04N 7/18* (2006.01)
*G01N 21/55* (2014.01)
*G01N 21/25* (2006.01)

(52) U.S. Cl.
CPC ............... *G01N 21/55* (2013.01); *G01N 21/25* (2013.01)

(58) Field of Classification Search
CPC .................................. G01N 21/55; C03C 25/00
USPC .......................................................... 348/88
See application file for complete search history.

(56) References Cited

U.S. PATENT DOCUMENTS

| | | |
|---|---|---|
| 2,535,830 A | 12/1950 | Beck |
| 3,524,983 A | 8/1970 | Voelz |
| 3,539,316 A | 11/1970 | Trethewey |
| 3,791,792 A | 2/1974 | Lindsay |
| 4,203,155 A | 5/1980 | Garst |
| 4,363,968 A | 12/1982 | McGowan et al. |
| 4,399,100 A | 8/1983 | Zsolnay et al. |
| 4,554,437 A | 11/1985 | Wagner et al. |
| 4,582,520 A | 4/1986 | Sturm |
| 4,609,628 A | 9/1986 | Aschenbeck |

(Continued)

FOREIGN PATENT DOCUMENTS

| | | |
|---|---|---|
| WO | 84/01430 | 4/1984 |
| WO | 12/078743 | 6/2012 |

(Continued)

OTHER PUBLICATIONS

International Search Report and Written Opinion, Application No. PCT/US12/34230 filed Apr. 19, 2012, Dated Jul. 17, 2012.

(Continued)

*Primary Examiner* — Andy Rao
*Assistant Examiner* — Tyler Edwards
(74) *Attorney, Agent, or Firm* — Calfee, Halter & Griswold LLP

(57) ABSTRACT

A method for assessing the cure status of a fibrous blanket manufactured with mineral fibers and binder is disclosed and comprises a using an online optical reflectance measurement as an assessment of cure status. The optical reflectance measurement may preferably be a color image taken of any surface, and in particular of a sectioned face, after which the image is optionally divided into multiple regions of interest (ROI) and analyzed for a color system variable that is representative of cure status. In some embodiments, the color system variable is the B value. Alternatively, the optical reflectance measurement may be UV or IR reflectance of a sectioned face. When two or more regions of interest are defined on a sectioned face, comparative information is valuable to assess cure at different levels, layers or portions of the interior of the fibrous product.

19 Claims, 7 Drawing Sheets

(56) References Cited

U.S. PATENT DOCUMENTS

| | | | |
|---|---|---|---|
| 4,769,544 A | 9/1988 | Dahlquist | |
| 5,142,151 A * | 8/1992 | Varnell et al. | 250/339.08 |
| 5,158,720 A | 10/1992 | Levy | |
| 5,206,918 A | 4/1993 | Levene | |
| 5,457,319 A | 10/1995 | Moe et al. | |
| 5,556,578 A | 9/1996 | Berneburg et al. | |
| 5,596,268 A | 1/1997 | Strong et al. | |
| 5,633,313 A | 5/1997 | Blanchard et al. | |
| 5,635,845 A | 6/1997 | Strong et al. | |
| 5,707,587 A | 1/1998 | Blanchard et al. | |
| 5,932,665 A | 8/1999 | DePorter et al. | |
| 6,099,162 A | 8/2000 | Walsh | |
| 6,168,064 B1 | 1/2001 | Berkin | |
| 6,331,350 B1 | 12/2001 | Taylor et al. | |
| 6,699,945 B1 | 3/2004 | Chen et al. | |
| 6,867,421 B1 * | 3/2005 | Hunt et al. | 250/461.1 |
| 6,884,849 B2 | 4/2005 | Chen et al. | |
| 7,063,983 B2 | 6/2006 | Chen | |
| 7,313,270 B2 | 12/2007 | Sones | |
| 7,435,444 B2 | 10/2008 | Freeman et al. | |
| 7,435,600 B2 | 10/2008 | Packard | |
| 7,520,188 B2 | 4/2009 | Calicott et al. | |
| 7,642,306 B2 | 1/2010 | Charbonneau et al. | |
| 7,718,214 B2 | 5/2010 | Charbonneau | |
| 7,781,512 B2 | 8/2010 | Charbonneau et al. | |
| 7,803,309 B2 | 9/2010 | Pado et al. | |
| 2001/0006264 A1 | 7/2001 | Wit et al. | |
| 2002/0022422 A1 | 2/2002 | Waldrop et al. | |
| 2002/0027074 A1 | 3/2002 | Tominaga et al. | |
| 2002/0146657 A1 | 10/2002 | Anderson et al. | |
| 2003/0103199 A1 * | 6/2003 | Jung et al. | 356/73 |
| 2003/0108662 A1 | 6/2003 | Rodenbaugh et al. | |
| 2003/0224527 A1 | 12/2003 | Chen | |
| 2005/0287675 A1 * | 12/2005 | Packard | 436/85 |
| 2006/0005580 A1 | 1/2006 | Espiard et al. | |
| 2006/0009569 A1 | 1/2006 | Charbonneau et al. | |
| 2006/0019024 A1 | 1/2006 | Freeman et al. | |
| 2006/0123914 A1 | 6/2006 | Pena et al. | |
| 2006/0249885 A1 | 11/2006 | Stacey | |
| 2007/0287018 A1 | 12/2007 | Tutin et al. | |
| 2008/0156041 A1 | 7/2008 | Cooper | |
| 2009/0007644 A1 | 1/2009 | Freeman et al. | |
| 2010/0001422 A1 | 1/2010 | Kulprathipanja et al. | |
| 2010/0068103 A1 | 3/2010 | Charbonneau et al. | |
| 2011/0086567 A1 | 4/2011 | Hawkins et al. | |
| 2012/0144868 A1 | 6/2012 | Mirth et al. | |
| 2012/0144870 A1 | 6/2012 | Johnson et al. | |
| 2012/0145035 A1 | 6/2012 | Shallenberger | |
| 2012/0146252 A1 | 6/2012 | Hawkins et al. | |
| 2012/0268586 A1 | 10/2012 | Yousef | |
| 2012/0271445 A1 | 10/2012 | Li | |
| 2012/0271588 A1 | 10/2012 | Li | |
| 2013/0152637 A1 | 6/2013 | Mirth et al. | |
| 2013/0152638 A1 | 6/2013 | Johnson et al. | |
| 2013/0306872 A1 | 11/2013 | Paulson | |

FOREIGN PATENT DOCUMENTS

| | | |
|---|---|---|
| WO | 12/145498 | 10/2012 |
| WO | 12/145500 | 10/2012 |

OTHER PUBLICATIONS

Office action from U.S. Appl. No. 13/313,072 dated Aug. 2, 2013.
Kam et al, "Optimal parameters for curing graphite/epoxy composite laminates", J. of materials Processing Technology, vol. 48, pp. 357-363 (1995).
Office action from U.S. Appl. No. 13/116,611 dated Aug. 15, 2013.
International Search Report and Written Opinion from PCT/US11/063720 dated Apr. 2, 2012.
International Search Report and Written Opinion from PCT/US12/34230 dated Jul. 17, 2012.
International Search Report and Written Opinion from PCT/US12/34234 dated Sep. 21, 2012.
Zheng (Ed.) Model Predictive Controll, Sciyo, 2010 (downloadable at: http://www.intechopen.com/books/show/title/model-predictive-control).
Badgwell & Qin, Industrial Model Predictive Control—An Updated Overview, presentation Mar. 9, 2002 (cited at: http://www.nt.ntnu.no/users/skoge/presentation/mpc_badgwell/mpc_survey_hand-out.pdf.
Office action from New Zealand Application No. 612,057 dated Apr. 8, 2014.
Office action from U.S. Appl. No. 13/317,071 dated Feb. 20, 2014.
Notice of Allowance from U.S. Appl. No. 13/116,611 dated Feb. 12, 2014.
Office action from New Zealand Application No. 616,917 dated Jul. 10, 2014.
Office action from New Zealand Application No. 616,726 dated Jul. 10, 2014.
Search Report from European Application No. 12773636.1 dated Feb. 16, 2015.
Office action from U.S. Appl. No. 13/313,071 dated Mar. 18, 2015.
Perkin Elmer, one page printout, Aluminum Sample Pans and Covers, accessed Mar. 12, 2015.
Kootsookos et al., "The effect of the degree of cure on the corrosion resistance of vinyl ester/glass fibre composites", Composites: Part A 35, pp. 501-508 (2004).
Office action from U.S. Appl. No. 13/313,071 dated Aug. 22, 2014.
Office action from Chinese Application No. 201280019475.4 dated Aug. 1, 2014.
Office action from Chinese Application No. 201280025633.7 dated Oct. 15, 2014.
Search Report from European Application No. 12773699.9 dated Feb. 12, 2015.
Office action from Australian Application No. 2012245484 dated Jan. 23, 2015.
Search Report from European Patent Application No. 12773636.1 dated Feb. 16, 2015.
Office action from Chinese application No. 201180059776.5 dated Feb. 4, 2015.
Office action from U.S. Appl. No. 13/288,302 dated Jan. 5, 2015.

* cited by examiner

METHOD FOR ONLINE DETERMINATION OF CURE STATUS OF GLASS FIBER PRODUCTS

CROSS-REFERENCE TO RELATED APPLICATIONS

This application is related to co-owned provisional application 61/421,295 filed Dec. 9, 2010, which is incorporated by reference.

BACKGROUND

This invention relates in general to insulation products made from fibrous minerals like glass and, in particular, to quality control methods for determining the cure status, i.e. whether the product is undercured, overcured or properly cured within specifications and process control limits.

Fibrous glass insulation products generally comprise randomly-oriented glass fibers bonded together by a cured thermosetting polymeric material. Molten streams of glass are drawn into fibers of random lengths and blown into a forming chamber or hood where they are randomly deposited as a pack onto a porous, moving conveyor or chain. The fibers, while in transit in the forming chamber and while still hot from the drawing operation, are sprayed with an aqueous dispersion or solution of binder. The residual heat from the glass fibers and combustion gases, along with air flow during the forming operation, are sufficient to vaporize and remove much of the sprayed water, thereby concentrating the binder dispersion and depositing binder on the fibers as a viscous liquid with high solids content. Ventilating blowers create negative pressure below the conveyor and draw air, as well as any particulate matter not bound in the pack, through the conveyor and eventually exhaust it to the atmosphere. The uncured fibrous pack is transferred to a drying and curing oven where a gas, heated air for example, is blown through the pack to dry the pack and cure the binder to rigidly bond the glass fibers together in a random, three-dimensional structure, usually referred to as a "blanket." Sufficient binder is applied and cured so that the fibrous pack can be compressed for packaging, storage and shipping, yet regains its thickness—a process known as "loft recovery"—when compression is removed.

While manufacturers strive for rigid process controls, the degree of binder cure throughout the pack may not always be uniform for a variety of reasons. Irregularities in the moisture of the uncured pack, non-uniform cross-machine weight distribution of glass, irregularities in the flow or convection of drying gasses in the curing oven, uneven thermal conductance from adjacent equipment like the conveyor, and non-uniform applications of binder, among other reasons, may all contribute to areas of over- or under-cured binder. Thus it is desirable to test for these areas in final product to assure quality.

U.S. Pat. No. 4,363,968 to McGowan, et al.; U.S. Pat. No. 4,582,520 to Sturm; and U.S. Pat. No. 4,609,628 to Aschenbeck, all teach methods of using multiple wavelengths of infrared ("IR") radiation to monitor the amount of binder or the degree of cure of the binder in a fiberglass mat product. In general, they all rely on differences in the IR absorption/transmission between the binder chemical reactants (carboxylic acid groups and alcoholic groups) and the cured binder products (ester groups). U.S. Pat. No. 4,769,544 to Dahlquist, and U.S. Pat. No. 7,435,600 to Packard are similar, except they rely on different wavelengths of IR and/or different ratios of reactants/products.

U.S. Pat. No. 7,520,188 discloses a destructive, off-line method of dying and scanning a fiberglass product, and performing a color analysis of red pixel ratio to determine a degree of cure.

While each of these methods had advantages, there are also drawbacks. The IR methodologies to date rely on transmission of radiation through the fibrous pack in one direction and thus are not capable of providing information about cure at various depths of the pack.

SUMMARY OF THE INVENTION

This invention relates generally to methods for assessing the cure status of a fibrous blanket manufactured with mineral fibers and binder. In a first important aspect, the invention comprises a method of determining the cure status of a mineral fibrous product that relies on capturing a color digital image of a any surface and analyzing the image. The method comprises:

capturing a color digital image from a surface of a fibrous product using a color digital camera;

analyzing at least one region of interest from said color digital image to obtain a color system variable for the region of interest; and assessing the degree of cure of the fibrous product on the basis the color system variable from the region of interest.

In this aspect, the color digital image may be captured from a surface that is an uncut exterior surface of the fibrous product or from a cut or sectioned face of the fibrous product. If the surface is a sectioned face, it may be sectioned or split longitudinally, or chopped transversely or even separated horizontally. It may, but does not need to be, performed continuously online without removing product from the manufacturing line for testing. Other variations are described below.

In a second important embodiment, the invention comprises a method of determining the cure status of a mineral fibrous product that does not require a color image, but may rely on any optical reflectance from a cut or interior face of the fibrous product. In this aspect, the method comprises:

capturing an optical reflectance measurement from the face of a sectioned fibrous product;

analyzing the optical reflectance measurement from at least one region of interest from the sectioned face; and assessing the degree of cure of the fibrous product on the basis the optical reflectance measurement at the region of interest.

The method according to this second aspect relies on the improved results obtained when looking into the interior of the fibrous product to determine cure. The optical reflectance measurement may be a color digital image, but it may also comprise other spectrometric measurements, such as UV or IR reflectance. In this aspect, the measurement may be from one region of interest or from multiple regions of interest. It may, but does not need to be, performed continuously online without removing product from the manufacturing line for testing. Other variations are described below.

In a third important aspect, the method involves determining the cure status of a mineral fibrous product by analyzing optical reflectance properties from at least two distinct regions of interest of any surface, preferably a cut interior surface. This third aspect comprises:

capturing an optical reflectance measurement from a surface of a fibrous product;

analyzing the optical reflectance measurement from at least two regions of interest from the surface; and assessing the degree of cure of the fibrous product on the basis the optical reflectance measurements at the at least two regions of interest.

In this third aspect, the at least two regions of interest may be from different positions in the Y direction, the X direction, or both; and may involve multiple regions of interest in multiple directions. The optical reflectance measurement may be a color digital image, but it may also comprise other spectrometric measurements, such as UV or IR reflectance. It may, but does not need to be, performed continuously online without removing product from the manufacturing line for testing. Other variations are described below.

There are several variations on any of the three aspects described above. When the reflectance measurement or color image is taken of a sectioned or interior face, it may be sectioned or split longitudinally, producing an X-Z plane for reflectance; or chopped transversly producing a Y-Z plane for reflectance; or even sectioned horizontally producing an X-Y plane for reflectance. he method of claim 20 further comprising analyzing at least 3 regions of interest in any direction.

In some aspects and embodiments, multiple regions of interest are analyzed. When this occurs, at least two distinct regions or interest are identified differing in position along at least one dimension, X, Y or Z; for example at least two regions in the X direction, at least 2 regions in the Y direction, at least two regions in the Z direction. The number of multiple regions in any given dimension may be 2, 3, 4, 5, 6, or more up to N=100. Additionally, there may be multiple regions in two dimensions simultaneously, thus creating a grid of multiple regions in a plane defined by the two dimensions, such as multiple regions in both the Z and Y direction of a chopped face. Such grids may have the same or different number of regions in each dimension and may be, for example: 2×2; 2×3; 2×4; 2×N; 3×3, 3×4; 3×5; 3×N; 4×4; 4×5; 4×6; 4×N, etc. up to as large as N×N if desired.

In some aspects and embodiments, the optical reflectance measurement is a digital color image. When this occurs, the analysis of the regions(s) of interest may comprise obtaining a value for at least one variable of a color variable system for each region of interest. Many different color variable systems may be used and are described herein, but one embodiment uses a LAB color system and the method comprises obtaining at least one; of (a) the A-value, (b) the B-value and/or (c) the L value of the LAB color system. Other systems are also envisioned.

Process control decisions that may be made include adjusting the process control to bring the process back within the predetermined process control limits, and this may be accomplished in either the oven or the forming hood area. For example, a process adjustment might mean adjusting in at least one zone of a curing oven an oven parameter selected from temperature and air flow in the oven zone. Alternatively, a process adjustment might mean adjusting at least one forming area parameter selected from coolant flow, binder flow, air flow, and weight distribution variables (or lapping system variables).

Various aspects of this invention will become apparent to those skilled in the art from the following detailed description of the preferred embodiment, when read in light of the accompanying drawings.

DETAILED DESCRIPTION

Figure 1:
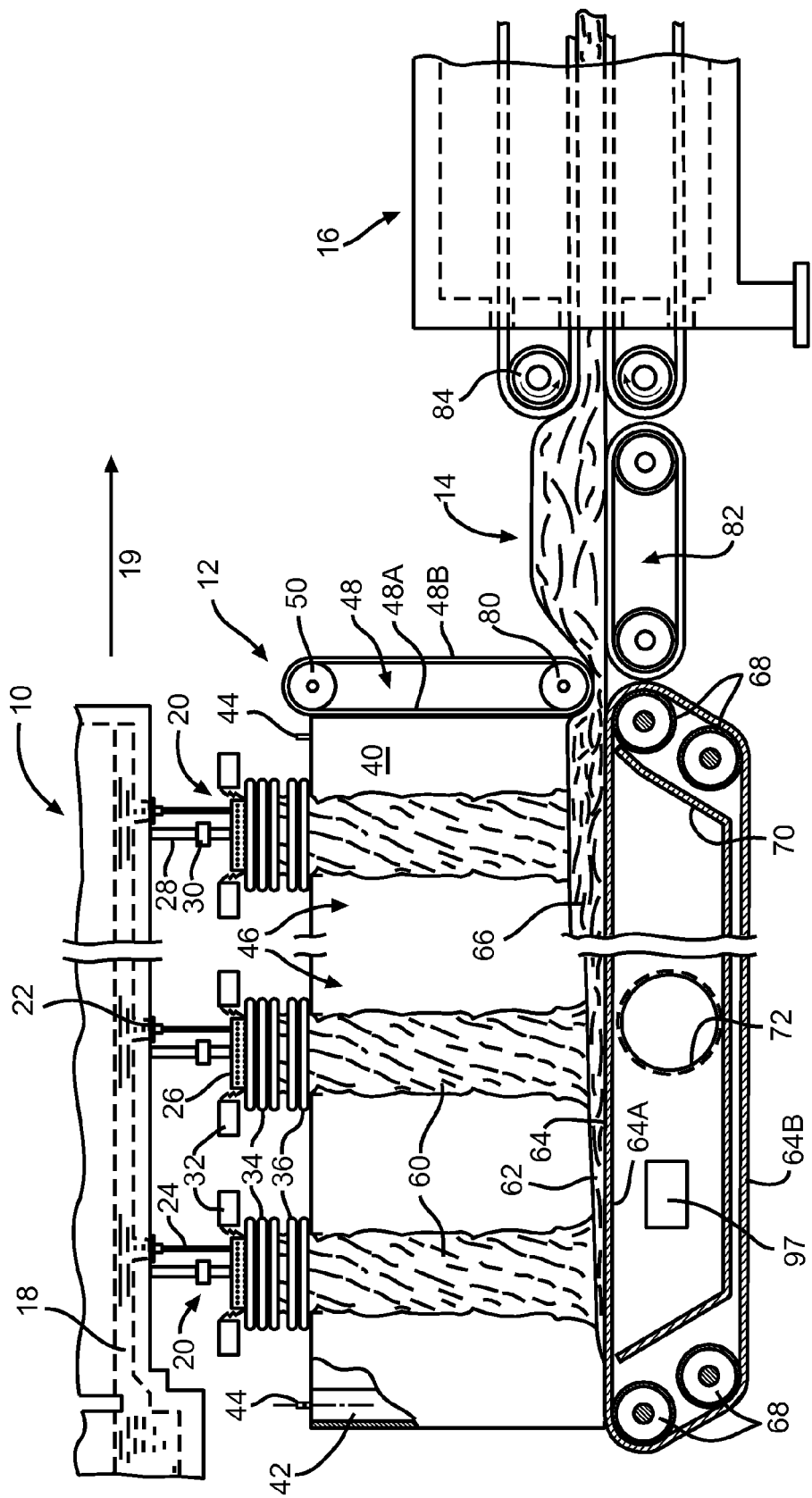
FIG. 1 is a partially sectioned side elevation view of a forming hood component of a manufacturing line for manufacturing fibrous products.

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are described herein. All references cited herein, including books, journal articles, published U.S. or foreign patent applications, issued U.S. or foreign patents, and any other references, are each incorporated by reference in their entireties, including all data, tables, figures, and text presented in the cited references.

In the drawings, the thickness of the lines, layers, and regions may be exaggerated for clarity.

Unless otherwise indicated, all numbers expressing ranges of magnitudes, such as angular degrees or sheet speeds, quantities of ingredients, properties such as molecular weight, reaction conditions, and so forth as used in the specification and claims are to be understood as being modified in all instances by the term "about." Accordingly, unless otherwise indicated, the numerical properties set forth in the specification and claims are approximations that may vary depending on the desired properties sought to be obtained in embodiments of the present invention. Notwithstanding that the numerical ranges and parameters setting forth the broad scope of the invention are approximations, the numerical values set forth in the specific examples are reported as precisely as possible. Any numerical values, however, inherently contain certain errors necessarily resulting from error found in their respective measurements. All numerical ranges are understood to include all possible incremental sub-ranges within the outer boundaries of the range. Thus, a range of 30 to 90 degrees discloses, for example, 35 to 50 degrees, 45 to 85 degrees, and 40 to 80 degrees, etc.

"Binders" are well known in the industry to refer to thermosetting organic agents or chemicals, often polymeric resins, used to adhere glass fibers to one another in a three-dimensional structure that is compressible and yet regains its loft when compression is removed. "Binder delivery" refers to the mass or quantity of "binder chemical" e.g. "binder solids" delivered to the glass fibers. This is typically measured in the industry by loss on ignition or "LOI," which is a measure of the organic material that will burn off the fibrous mineral. A fibrous pack is weighed, then subjected to extreme heat to burn off the organic binder chemical, and then reweighed. The weight difference divided by the initial weight (×100) is the % LOI.

As solids, rate of binder delivery is properly considered in mass/time units, e.g. grams/minute. However, binder is typically delivered as an aqueous dispersion of the binder chemical, which may or may not be soluble in water. "Binder dispersions" thus refer to mixtures of binder chemicals in a medium or vehicle and, as a practical matter, delivery of binder "dispersions" is given in flow rate of volume/time. e.g.

liters/minute or LPM of the dispersion. The two delivery expressions are correlated by the mass of binder per unit volume, i.e. the concentration of the binder dispersion. Thus, a binder dispersion having X grams of binder chemical per liter flowing at a delivery rate of Z liters per min delivers X*Z grams/minute of binder chemical. Dispersions include true solutions, as well as colloids, emulsions or suspensions.

References to "acidic binder" or "low pH binder" mean a binder having a dissociation constant (Ka) such that in an aqueous dispersion the pH is less than 7, generally less than about 6, and more typically less than about 4.

"Mineral fibers" refers to any mineral material that can be melted to form molten mineral that can be drawn or attenuated into fibers. Glass is the most commonly used mineral fiber for fibrous insulation purposes and the ensuing description will refer primarily to glass fibers, but other useful mineral fibers include rock, slag and basalt.

"Product properties" refers to a battery of testable physical properties that insulation batts possess. These may include at least the following common properties:

"Recovery"—which is the ability of the batt or blanket to resume it's original or designed thickness following release from compression during packaging or storage. It may be tested by measuring the post-compression height of a product of known or intended nominal thickness, or by other suitable means.

"Stiffness" or "sag"—which refers to the ability of a batt or blanket to remain rigid and hold its linear shape. It is measured by draping a fixed length section over a fulcrum and measuring the angular extent of bending deflection, or sag. Lower values indicate a stiffer and more desirable product property. Other means may be used.

"Lateral weight distribution" (LWD or "cross weight")—which is the relative uniformity or homogeneity of the product throughout its width. It may also be thought of as the uniformity of density of the product, and may be measured by sectioning the product longitudinally into bands of equal width (and size) and weighing the band, by a nuclear density gauge, or by other suitable means.

"Vertical weight distribution" (VWD)—which is the relative uniformity or homogeneity of the product throughout its thickness. It may also be thought of as the uniformity of density of the product, and may be measured by sectioning the product horizontally into layers of equal thickness (and size) and weighing the layers, by a nuclear density gauge, or by other suitable means.

Of course, other product properties may also be used in the evaluation of final product, but the above product properties are ones found important to consumers of insulation products.

FIG. 1 illustrates a glass fiber insulation product manufacturing line including a forehearth 10, forming hood component or section 12, a ramp conveyor section 14 and a curing oven 16. Molten glass from a furnace (not shown) is led through a flow path or channel 18 to a plurality of fiberizing stations or units 20 that are arranged serially in a machine direction, as indicated by arrow 19 in FIG. 1. At each fiberizing station, holes 22 in the flow channel 18 allow a stream of molten glass 24 to flow into a spinner 26, which may optionally be heated by a burner (not shown). Fiberizing spinners 26 are rotated about a shaft 28 by motor 30 at high speeds such that the molten glass is forced to pass through tiny holes in the circumferential sidewall of the spinners 26 to form primary fibers. Blowers 32 direct a gas stream, typically air, in a substantially downward direction to impinge the fibers, turning them downward and attenuating them into secondary fibers that form a veil 60 that is forced downwardly. The fibers are distributed in a cross-machine direction by mechanical or pneumatic "lappers" (not shown), eventually forming a fibrous layer 62 on a porous conveyor 64. The layer 62 gains mass (and typically thickness) with the deposition of additional fiber from the serial fiberizing units, thus becoming a fibrous "pack" 66 as it travels in a machine direction 19 through the forming area 46.

One or more cooling rings 34 spray coolant liquid, such as water, on veil 60 to cool the fibers within the veil. Other coolant sprayer configurations are possible, of course, but rings have the advantage of delivering coolant liquid to fibers throughout the veil 60 from a multitude of directions and angles. A binder dispensing system includes binder sprayers 36 to spray binder onto the fibers of the veil 60. Illustrative coolant spray rings and binder spray rings are disclosed in US Patent Publication 2008-0156041 A1, to Cooper. Each fiberizing unit 20 thus comprises a spinner 26, a blower 32, one or more cooling liquid sprayers 34, and one or more binder sprayers 36. FIG. 1 depicts three such fiberizing units 20, but any number may be used. For insulation products, typically from two to about 15 units may be used in one forming hood component for one line.

The forming area 46 is further defined by side walls 40 and end walls 48 (one shown) to enclosed a forming hood. The side walls 40 and end walls 48 are each conveniently formed by a continuous belt that rotates about rollers 44 or 50, 80 respectively. The terms "forming hoodwall", "hoodwall" and "hood wall" may be used interchangeably herein. Inevitably, binder and fibers accumulate in localized clumps on the hoodwalls and, occasionally, these clumps may fall into the pack and cause anomalous dense areas or "wet spots" that are difficult to cure.

The conveyor chain 64 contains numerous small openings allowing the air flow to pass through while links support the growing fibrous pack. A suction box 70 connected via duct 72 to fans or blowers (not shown) are additional production components located below the conveyor chain 64 to create a negative pressure and remove air injected into the forming area. As the conveyor chain 64 rotates around its rollers 68, the uncured pack 66 exits the forming section 12 under exit roller 80, where the absence of downwardly directed airflow and negative pressure (optionally aided by a pack lift fan, not shown) allows the pack to regain its natural, uncompressed height or thickness s. A subsequent supporting conveyor or "ramp" 82 leads the fibrous pack toward an oven 16 and between another set of porous compression conveyors 84 for shaping the pack to a desired thickness for curing in the oven 16.

Figure 2:
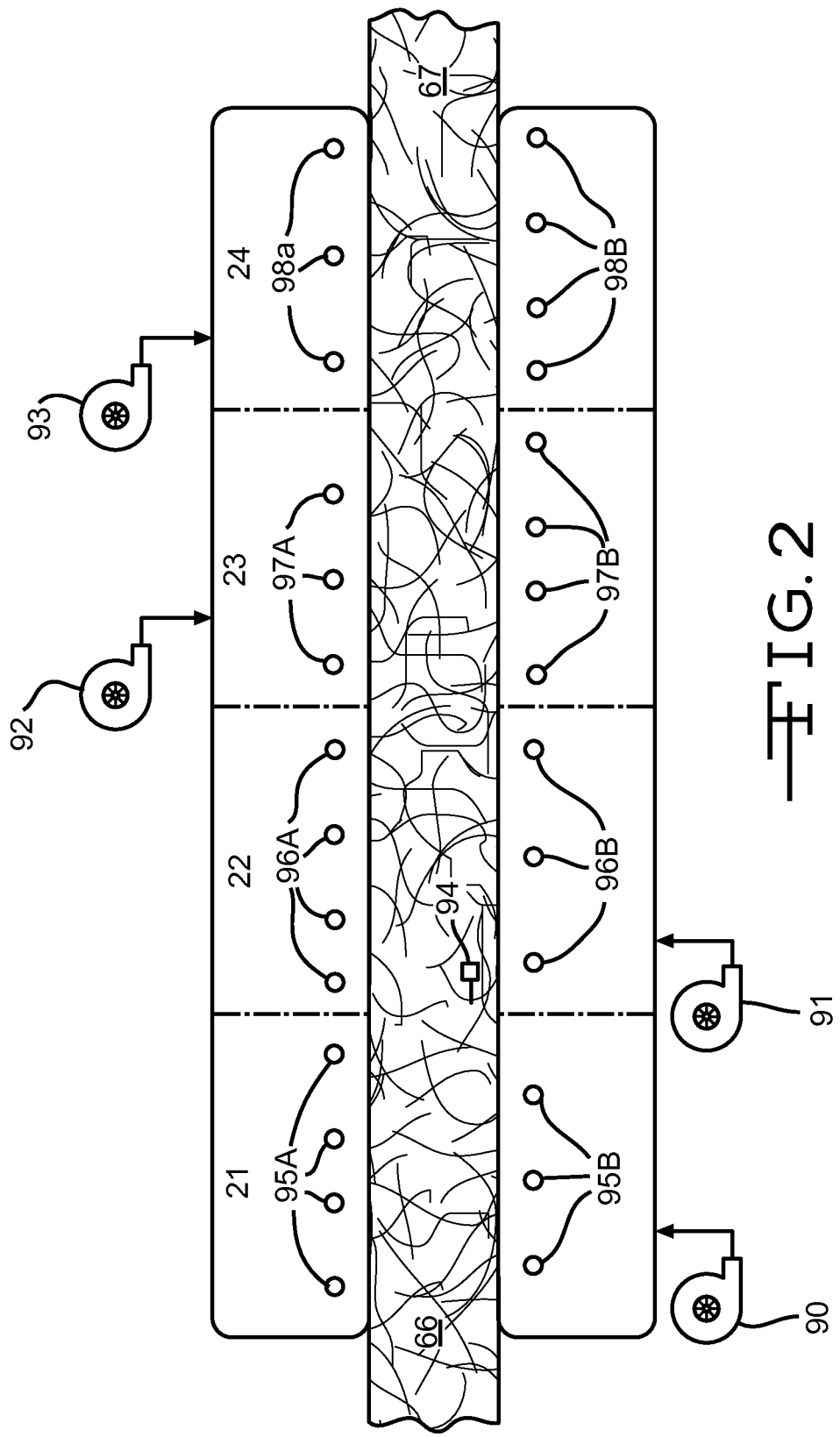
FIG. 2 is a schematic illustration representing the curing oven and its several zones.

FIG. 2 is a schematic diagram representing an oven 16 which typically may include four distinct zones, Z1, Z2, Z3 and Z4. The zones are designed to carry out multiple processes. In zones 1 and 2, fans 90, 91 blow a stream of warmed air upwards through the pack 66; while in zones 3 and 4, fans 92, 93 blow a stream of warmed air downwards through the pack 66. The choice of up versus down draft is preference, but upward is often used first to help counteract the downward suction force present in the forming hood. The air is heated by any suitable means, such as gas burners (not shown) associated with each zone to a temperature in the range of from about 400 F to about 600 F. In some embodiments, zones 1 and 2 are generally heated to a temperature of about 400 F to about 450 F, while zones 3 and 4 are heated to a temperature from about 430 F to about 550 F. Generally the initial zone(s) are used to drive out much of the moisture resident in the pack from the forming process, while later zones are used to finalize the curing of the binder.

Process controls include suitable control valves (not shown) for increasing or decreasing the temperature of each oven zone independently. In order to monitor the temperature of the oven, thermocouples may be installed. In some embodiments, a wireless thermocouple 94 may be inserted directly into the insulation pack prior to entry into the oven. Such a travelling thermocouple is referred to as a mole, and provides the best estimate of the actual pack temperature, but only at one location and only for as long as the pack is in the oven. Alternatively, thermocouples 95A-98A may be installed in the oven above the pack 66, and/or thermocouples 95A-98B may be installed below the pack 66. Although 3 or 4 thermocouples are shown above and below the pack 66 in each zone in FIG. 2, the number may vary from 1 to about 15 in each location, depending on the cross-sectional area and/or length of the zone. The thermocouples may, but need not be, aligned linearly in the X direction. By placing thermocouples in sets, some above (A) and some below (B) the pack, it is possible to obtain a proxy estimate of the temperature of the pack itself, such as by averaging the two readings. It is also possible to understand how much energy is absorbed by the pack in evaporating the moisture from it or in carrying out the curing reaction. This is advantageous over a mole thermocouple in that real-time pack temperature data is available on a continuous basis.

With dual thermocouples (A-B) on either side of the pack and taking into account the up or downdraft nature of airflow in each zone, it is useful think of lower thermocouples 95B and 96B as "upstream" or "inlet" thermocouples since they monitor the temperature of air as it enters the pack; and to think of upper thermocouples 95A and 96A as "downstream" or "exit" thermocouples since they monitor the temperature of air as it exits the pack. Conversely, because the flow is reversed in zones 3 and 4, lower thermocouples 97B and 98B can be thought of as "downstream" or "exit" thermocouples and upper thermocouples 97A and 98A can be thought of as "upstream" or "inlet" thermocouples. By using a mole in combination with stationary thermocouples in experiments, applicants have found that difference between the exit thermocouple in zone 1 and the exit thermocouple in zone 2 (delta T) can be used to infer moisture drying rate in the pack; while the exit temperature in the last two oven zones can be used to estimate the pack temperature once the pack is dry.

Upon exit from the oven 16, the cured pack or "blanket" 67 is conveyed downstream for cutting and packaging steps. For many products, the blanket is sectioned or "split" longitudinally into multiple pieces or lanes of standard width dimension, for example, 14.5 inch widths and 22.5 inch are standardized to fit in the space between 2×4 studs placed on 16 inch or 24 inch centers, respectively. Other standard widths may also be used. A blanket may be 4 to 8 feet in width and produce multiple such standard width pieces.

Blankets are typically also sectioned or "chopped" in a direction transverse to the machine direction for packaging. Transverse chopping divides the blanket lanes into shorter segments known as "batts" that may be from about 4 feet up to about 12 feet in length; or into longer, rolled segments that may be from about 20 feet up to about 175 feet or more in length. These batts and rolls may eventually be bundled for packaging. A faster-running takeup conveyor separates one batt from another after they are chopped to create a space between sectioned batt ends. If longitudinal "lanes" are desired, they generally are split prior to chopping into shorter lengths.

Figure 3:
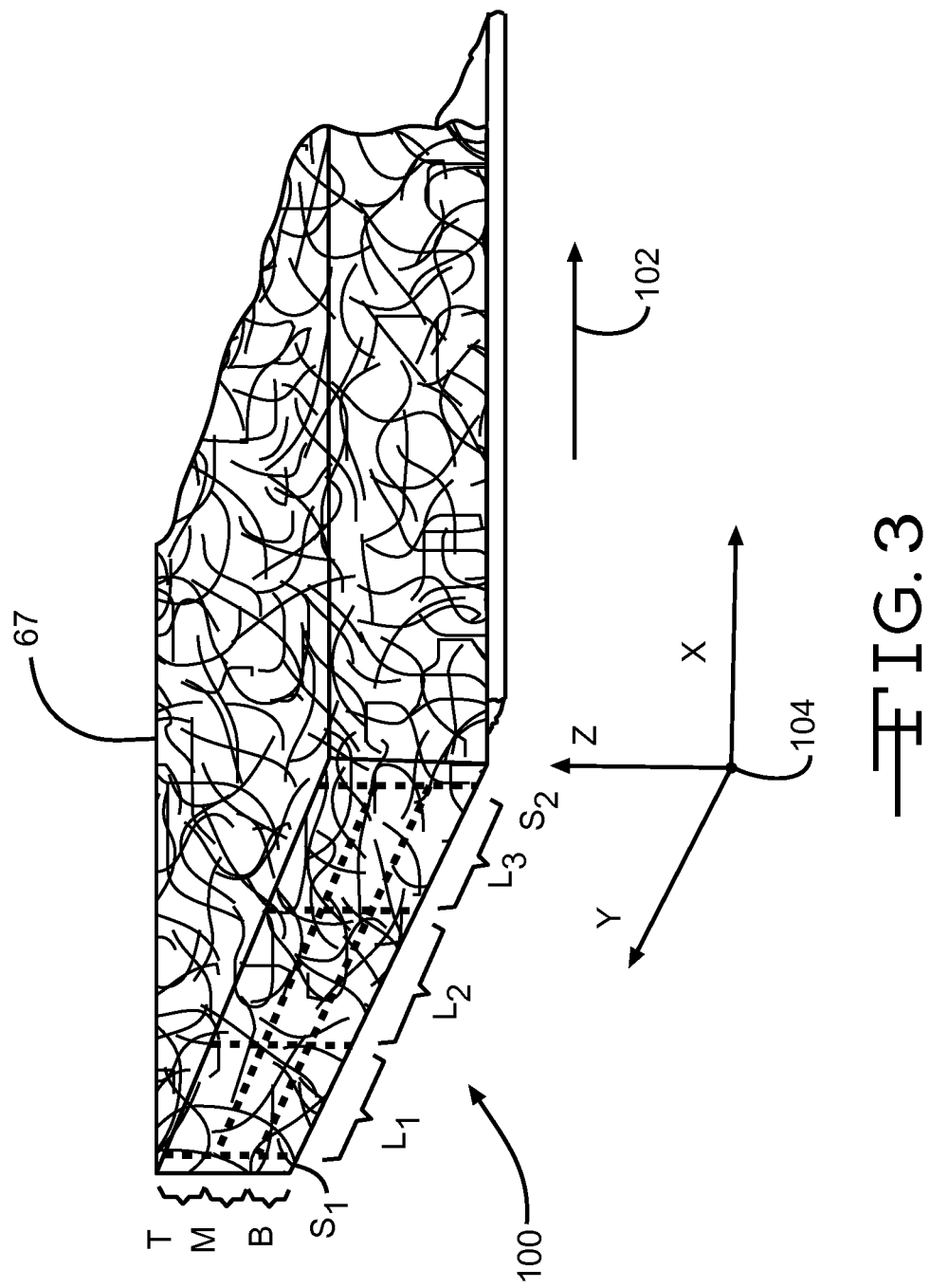
FIG. 3 is a perspective view of a fibrous product showing a sectioned face.

Referring to FIG. 3, a portion of a blanket 67 is shown after exiting the oven. It is useful to describe three dimensional aspects using the X, Y, Z coordinate system, and it is conventional in the industry to assign the X dimension to be the machine direction 102, the Y dimension to be the cross machine direction and the Z dimension to be the height or thickness direction as is shown by the axes depiction 104. As used herein, the term "section" is any cut into the interior of the blanket and in most cases is a straight or planar cut. However, the term "section" (and its derivatives like "sectioned" or "sectioning", etc.) includes cuts in any direction, including cuts that are parallel to the orthogonal axes planes and cuts that are not. A sectioned face that lies generally in the X-Z plane is also known as a longitudinal "split" and generally defines the "lanes" of specific width. In contrast, a section that lies generally in the Y-Z plane is also known as a "chopped" section. FIG. 3 illustrates a "chopped" section revealing end face 100 of the blanket, although the term "end face" encompasses either the leading or terminal face of a chopped blanket. The "chopped" section cut is transverse to the machine direction indicated by arrow 102. Finally, a section may include cuts in the X-Y plane or in planes not aligned with the XYZ axes.

As described below, one or more cameras capture an image of this end face 100 and, in some embodiments, processing software divides the image into a grid having at least two regions of interest ("ROIs"), preferably a plurality of ROIs, for example at least 3 ROIs in the vertical or Z direction. In FIG. 3, nine such ROIs are depicted: three rows designated T, M and B for top, middle and bottom, and three "lanes" designated L1, L2 and L3. The ROI lanes may, but do not have to, correspond to longitudinal sectioning of a wide blanket into standard width lanes as described above. Thus, each ROI may be described using row/column coordinates, much like a spreadsheet. In addition to the nine ROIs of FIG. 3, there are two side regions designated S1 on the left and S2 on the right. It is generally desirable to cut away and recycle side edges like this.

Figure 4A:
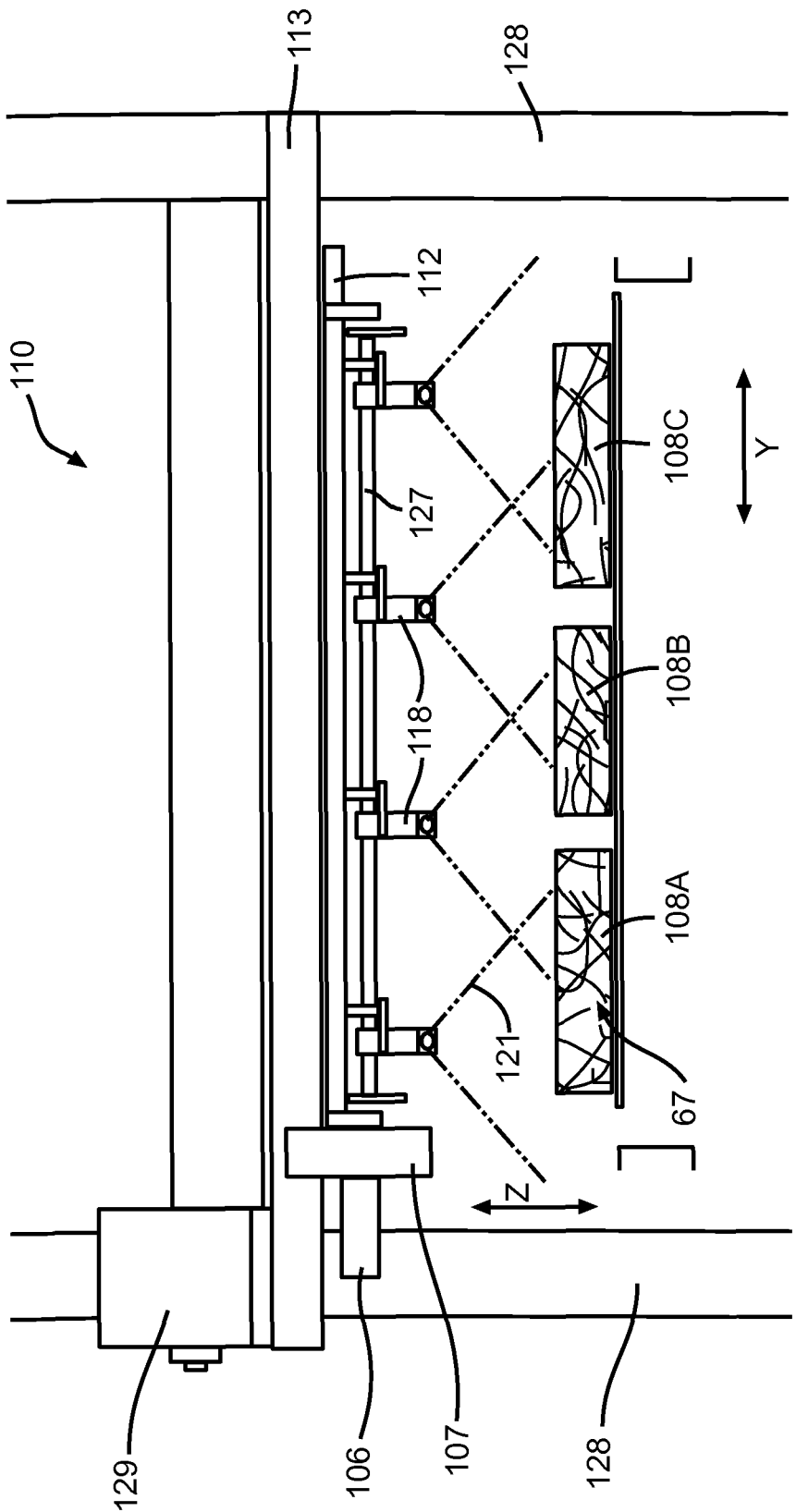
FIG. 4A is a front view of a camera system installed over a manufacturing line.
Figure 4B:
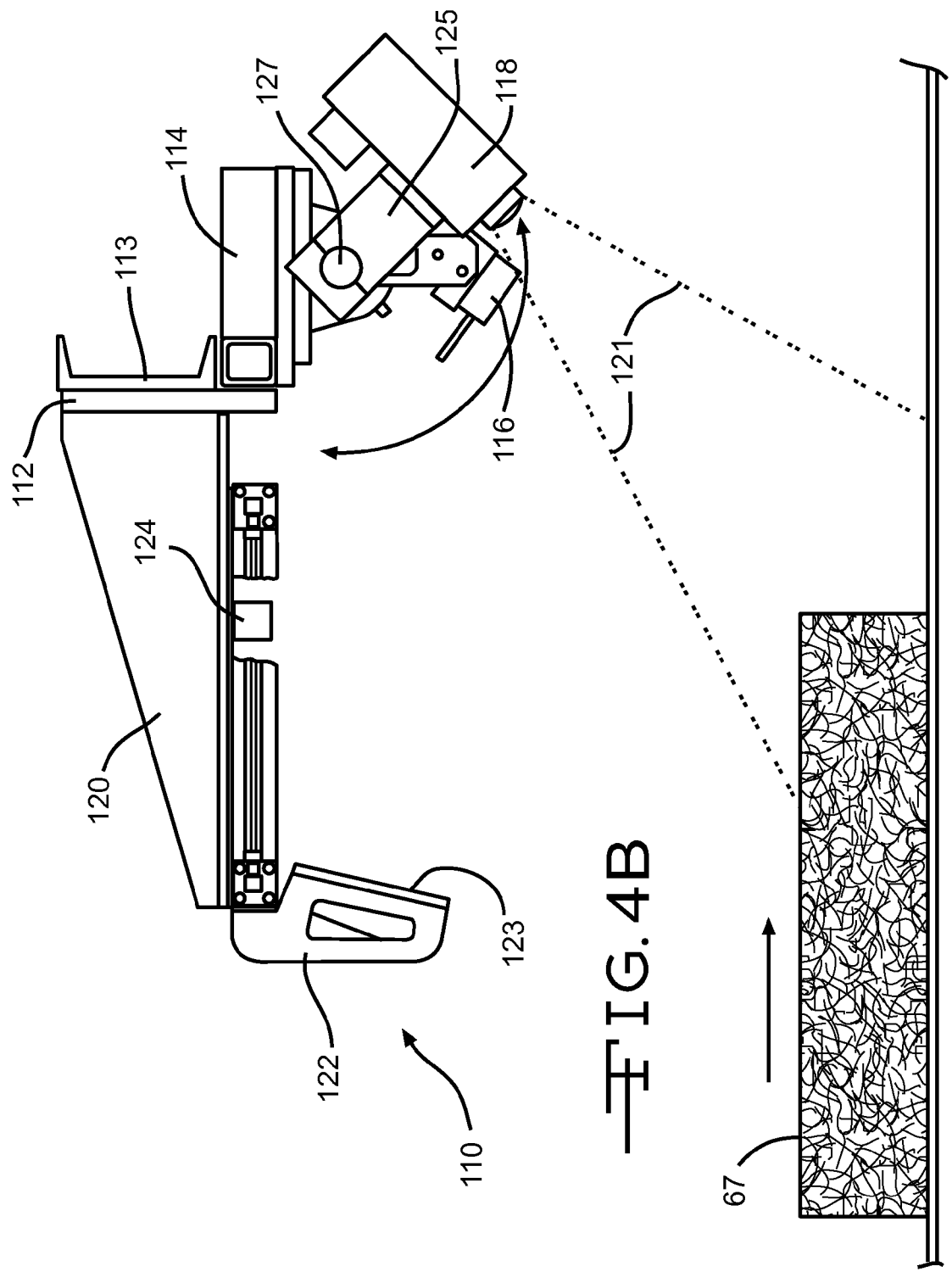
FIG. 4B is a side view of this system.

FIGS. 4A and 4B illustrate an image capture system 110 for capturing the image mentioned above. Upon exit from the oven 16, the cured blanket 67 is led past this image capture system 110, typically under it. As noted above, longitudinal splits may divide the blanket in to multiple lanes as represented by lanes 108A, 108B, and 108C. A mounting bracket 112 is suspended from a horizontal rail 113 extending over the manufacturing line. The bracket 112 has two ends. A first end (to the right in FIG. 4B) includes a camera arm 114, on which are secured illumination lights 116 and at least one camera 118. A second end of the mounting bracket 112 includes a calibration arm 120 on which is mounted a calibration plate 122 having a calibration surface 123 facing the camera 118. Either the camera arm 114 or the calibration plate 122, or both, is pivotably mounted so that it is permitted to swing upward/downward to place the calibration plate 122 into the view of the camera 118 for calibrating the camera. In FIG. 4B, a pivot bracket 125 is pivotably mounted to the camera arm 114 and pivots about pivot pin 127, so that the camera 118 can swing upward to capture a calibration image from the calibration plate surface 123. Motor 106 and gear box 107 are coupled to pivot shaft 127 to cause the rotation that pivots the cameras 118. The angle of view of each camera is represented by lines 121 extending from the camera lens which, depending on the thickness of the blanket 67, may overlap as shown.

Although a single camera is shown in FIG. 4B and described herein, the image capture system 110 may comprise an array of multiple cameras arranged side by side in the Y direction, as shown in FIG. 4A to capture the image of the sectioned face 100 across the entire width of the blanket 67 in the Y direction, as well as the entire height in the Z direction.

For example, a blanket of 4-6 feet in width may utilize 3 to 6 cameras, with sufficient lights 116 to capture a suitable image. Support towers 128 elevate the image system 110 above the manufacturing line as needed, and a control panel 129 may be installed on one side or the other. Additional brackets, arms and calibration plates may be added as needed to support the cameras and lights.

Mounted on the bracket 112 (shown behind a cutaway section of support strut) is a laser height sensor 124. This detects the height of the blanket, which may vary depending on the desired R value, and sends a binary (on/off) signal to a processor (not shown). When the height of the blanket is above a preset threshold, the sensor 124 sends the "on" signal; but when the height drops below the threshold (e.g. to zero relative to the conveyor, as when a gap between chopped batts is encountered), the sensor 124 sends an "off" signal to the processor. Either change (from off to on, or from on to off) can be used to trigger the camera 118 to capture an image, depending on the camera configuration. The end face 100 may be the trailing edge of a batt that has already passed, as depicted in FIG. 3, for which the on-to-off sensor signal change triggers the camera. Alternatively, the end face 100 may be the leading edge of a batt that is about to pass as in FIG. 4B, and the sensor off-to-on signal change triggers the camera. In either case, the angle of the camera 118 and the distance of the height sensor 124 from the blanket are coordinated to ensure that the camera captures an image of the sectioned end face 100. Any suitable gap or height or interruption sensor could be used in place of a laser sensor 124.

The illuminating lights 116 may comprise any means of illumination, including but not limited to incandescent, fluorescent and light emitting diodes (LED). They may be configured to be constantly on or they can be configures to flash or "strobe" in combination with the camera trigger. The color of "white" light is very subjective, thus the need for "white balancing" or color calibration of the cameras. However, it is desirable for the illumination to remain as constant as possible over time and temperature to minimize recalibration. The more the color or intensity shifts, the more frequently the cameras must be calibrated. Suitable illumination was obtained from Model L300 Linear Connect-a-Light available from Smart Vision Lights, Muskegon, Mich.; or from model number HBR-LW16, white LED light made by CCS America, Burlington, Mass. In some cases, one or two light bars were utilized. In some embodiments, the lights pivot with the camera, while in other embodiments, the lights are stationary.

The camera 118 in some embodiments is a charge coupled device (CCD) digital color camera. Resolution is not critical; successful operation was achieved with resolutions of 480× 640 as well as 1024×760, 1296×966, and 1392×1040. Manufacturers of suitable cameras include Sony, Hitachi, Basler, Toshiba, Teledyne Dalsa, and JAI.

Figure 5:
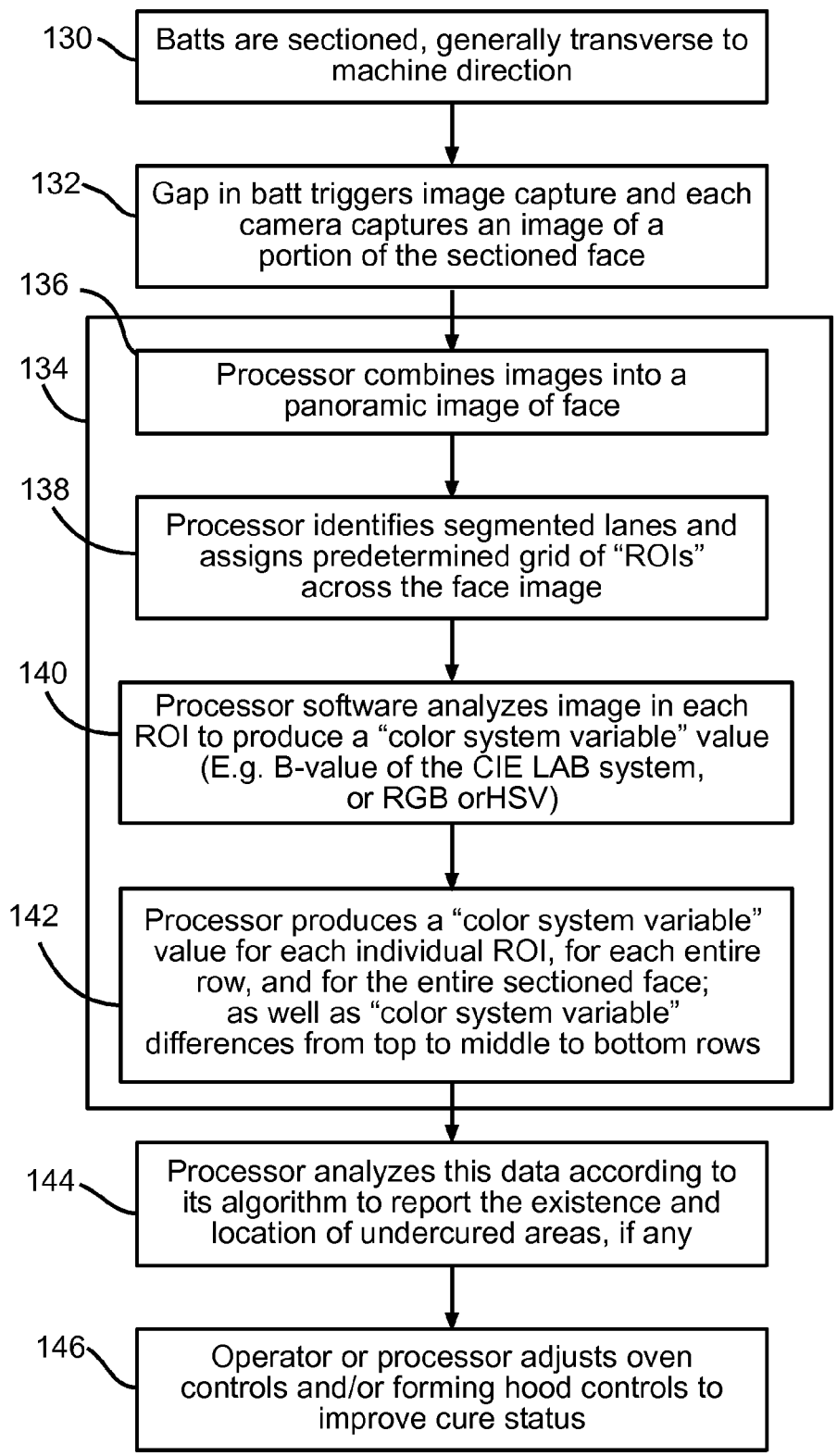
FIG. 5 is a block diagram representing the steps of one process embodiment according to the invention.

Various image processing software packages are commercially available and it is believed that many would be suitable for use with the invention. Exemplary image processing software programs include those from Cognex, Matrox, National Instrument, and Keyence. The generalized steps that the software may perform are set forth in a portion of the block diagram of FIG. 5. As mentioned above and represented by block 130, the blanket, or longitudinal slices thereof, are sectioned transversely to create leading and trailing end faces. The gap in blanket height triggers the camera or cameras to capture an image of the end face, block 132. This image is fed to a processor represented by block 134 where the software performs a suitable analysis of the image. If necessary, the processor combines multiple images into one panoramic view (block 136). If longitudinal sections are already cut into the blanket, the processor can identify the edges of the longitudinal sections and create boundaries of the image that correspond to the longitudinal lanes. The processor also overlays a grid of regions of interest (ROIs) onto the image, block 138. There should be at least 2 vertical ROIs for comparison, and preferably at least 3 ROIs in a vertical or Z direction. Horizontally (i.e. in the Y direction) there may be one or more ROIs. The Y-direction bounds of the ROI may correspond exactly to the segmented lanes, or there may be a plurality of horizontal ROIs per lane of the image. As mentioned above, FIG. 3 illustrates 9 total ROIs: 3 in the horizontal direction and 3 in the vertical direction.

The processor then analyzes each ROI to obtain a value for at least one color system variable, block 140. A wide variety of color system variables are useful and some are described below. The B-value is one color system variable that has been found suitable for monitoring the cure state of fibrous insulation products and is described herein as one example; although a variety of other color system variables might also be used. At least one color system variable is obtained for each ROI. If desired, the color system variable values from each ROI may be combined mathematically to find average, differential or blended values for larger areas, block 142. For example, in some embodiments, a color system variable value is calculated for all horizontal ROIs as a group, producing an average top color value, average middle color value and average bottom color value. Examining the subtractive difference between these helps assess whether the blanket is curing evenly top to bottom. Similarly, all vertical ROIs of a single lane may be averaged to assess the evenness of cure from right lanes to left lanes. Finally, in some embodiments, it may be useful to combine all ROIs together to assess an average cure of the entire end face.

Many software packages will also provide statistical measures of the variability of the data collected, such as minimum, maximum, range, mean, median, standard deviation, etc. It is assumed for discussion that only one color system variable is measured. While that may be sufficient, in some embodiments it may be desirable to measure from each ROI multiple color system variables (such as but not limited to L, A and B, see below) and statistical information for each value.

All the data is examined by the processor, which can report the existence and location of areas that may be undercured (or overcured), block 144. Subsequently, the operator can manually adjust process controls to improve the cure status, block 146. Alternatively, the processor may be programmed to make automatic process control adjustments. For example, right-to-left or side-to side variations (cross machine or Y direction) in cure might cause adjustment of the pneumatic lappers to achieve a more uniform weight distribution. The bottom layer is sometimes more cured due to a variety of possible reasons, including, e.g. upward convection of high temperature air in zones 1 and 2 of the oven and conduction of additional heat from the conveyor chain 64 as the pack traverses the oven. Undercured top areas (relative to middle or bottom) may suggest higher temperatures or higher fan speeds in zones 3 and 4 (which have downdraft airflow) or, conversely, by reducing the temperature or airflow in zones 1 and 2. Undercure in the middle ROI (relative to top and bottom) might suggest reducing moisture at middle forming units.

The mounting brackets and arms may be any suitable material, such as stainless steel or aluminum, for suspending the required equipment.

A key feature of the invention is the ability to see inside the pack to a "sectioned" or interior face on a continuous basis to examine cure state within the pack. This is very different from existing online systems that look only at the exterior surface, and from existing offline visual or color systems that cannot be performed on a continuous basis.

Many different color system variables are suitable for use with the invention. Due to physiological idiosyncrasies of the eye (sensitivity is not uniform across all wavelengths) there have been many different attempts to quantify color as humans perceive it, the details of which are not essential to the invention. However, some of the useful color space systems and the color system variables they utilize are set forth in the following table A.

TABLE A

Color system variable Systems and Descriptors

| Name | Description | Color system variables |
| --- | --- | --- |
| RGB | Color encoding scheme | red, green and blue (RGB) color |
| HSL | Color encoding scheme | Hue, Saturation, and Luminance |
| HSV | Color encoding scheme | Hue, Saturation, and Value |
| HSI | Color encoding scheme | Hue, Saturation, and, Intensity |
| Hunter LAB | Color encoding scheme based on knowledge that eye reacts more to luminance than hue | L (perceived luminosity); A (color position between red/magenta and green); and B (color position between yellow and blue) |
| CIE XYZ | Color encoding scheme that transforms RGB system to one using only positive values | x, y, z corresponding to hue, chroma and lumnosity |
| CIE L*a*b* or CIELAB | Color encoding scheme that modifies Hunter according to the human vision system by mimicking the logarithmic response of the eye | L or L* (perceived luminosity); A or a* (color position between red/magenta and green); and B or b* (color position between yellow and blue) |
| CIE L*u*v* or CIELUV | Color encoding scheme that classifies colors according proportional perceptual differences | L* (perceived luminosity); u* (chroma); and v* (hue); like XYZ |
| YIQ | For TV broadcasting, linear transform of RGB assigning greater bandwidth to luminance | Y is similar to perceived luminance, I and Q carry color information and some luminance information |

CIE stands for Commission internationale de l'éclairage, or the International Commission on Illumination.

Many if not all of the color system variables for above systems can be mathematically derived from the values of other systems. This facilitates measurements, since only one set of values need be measured, for example RGB, and many of the other color system variables can be calculated. As noted above, in some embodiments one need only measure a single color system variable, while in other embodiments multiple color system variables are measured. Multiple measurements may take into consideration all the color system variables of the system or a subset of all the values. The LAB systems have been found particularly useful, and one can measure and use all three values: L (perceived luminosity); A (a color position between red/magenta and green); and B (a color position between yellow and blue); just one value, such as the L, A or B value; or a combination of two values.

While the invention has been described using the preferred optical measurement of color system variable measured in at least two ROIs on a sectioned end face, it should be appreciated that the invention encompasses other broader embodiments in two areas. In a first broad aspect, the invention comprises an online method of capturing and analyzing a color image from any surface of a fibrous product on a periodic basis without destroying the product. By "online" is meant that the measurements are taken without removing a sample of the fibrous product from the manufacturing line. Online measurements are essentially continuous in that every batt can be sampled if desired without destruction or loss of line speed; although each captured image remains a still photo or snapshot. The sectioned end is advantageous because it affords a view of the interior of the product, but the sectioned end is not essential in this aspect and color images may be captured of other surfaces in an online process according to the invention.

In a further broad aspect, the invention comprises the use of optical reflectance measurements other than color images taken of sectioned faces. Digital color images are preferred and imply the use of reflectance in the visible range of the electromagnetic spectrum. However, the invention also contemplates the use of reflectance of other electromagnetic radiation, including infrared (IR) and ultraviolet (UV) regions of the electromagnetic spectrum. Thus, spectrometer-like IR or UV reflectance of at least a portion of a sectioned face can produce data useful for analysis of cure status in accordance with the invention. In other embodiments, the reflectance measurement may be taken from an uncut surface.

In a further broad aspect, the invention comprises the use of multiple optical reflectance measurements taken of any faces of a blanket. While online spectrometer-like reflectance has been utilized in the past on single location of a top surface, this has not, to our knowledge, been extended to side surfaces, bottom surfaces or to combinations of these involving multiple reflectance measurements. For example data useful for analysis of cure status in accordance with the invention may be obtained by spectrometer reflectance measurements from two side-by-side locations in the Y direction, from top and bottom surfaces, and/or from multiple locations in a Z direction along the side surface.

With at least one optical reflectance measurement of cure assessment in hand, the cure status of the pack or batt is known with a higher degree of accuracy, including information about the degree or magnitude of undercure or overcure, if any. This provides the manufacturer with valuable and actionable data with which to adjust the process controls as needed. For example, manufacturers have predetermined product specifications and product not falling within those ranges is said to be "out of spec" and must generally be scrapped or recycled. Moreover, most manufacturers have process controls and set predetermined limits to the variability of their processes. These parameters, along with illustrative values for one type of product, are summarized in the following Table B.

TABLE B

Manufacturing Limits

| Abbreviation | Term and meaning | Illustrative B-value* |
|---|---|---|
| USL | Upper Specification Limit - the value above which product is out of spec and must be discarded or scrapped. | 12-15 |
| UCL | Upper Control Limit - the value above which product is outside of the preset limits of acceptable process variability, although it may still be within spec. | 8-10 |
| LCL | Lower Control Limit - the value below which product is outside of the preset limits of acceptable process variability, although it may still be within spec. | 4-6 |
| LSL | Lower Specification Limit - the value below which product is out of spec and must be discarded or scrapped. | 2-3 |

*stated B-values are for light to medium density insulation with pink dye added. Without pink dye or for higher density products the concept is the same, but actual values may be shifted.

Knowing the cure status quantitatively in relation to these limits has significant consequences for the manufacturer. As noted above, product that is "out of spec" is generally scrapped or recycled. But if the only information available to the manufacturer is that the product is undercured—then a manufacturer may scrap product unnecessarily if it was low but still above a LSL. More specifically, product testing outside the USL and LSL still must be scrapped, but product testing between the USL and UCL, or between the LCL and LSL may still be used and not scrapped. This is valuable information, since the manufacturer will incorrectly scrap good product less frequently.

Perhaps even more importantly, the manufacturer now gains quantitative information about how far the product is from any of the limits mentioned above. Previously, if product was within specification it was retained and the process was deemed acceptable and not necessarily adjusted. Product testing outside the Control Limits (i.e. >UCL or <LCL) but still within spec (i.e. >LSL and <USL) gives the manufacturer the opportunity to adjust process controls to try to bring the process back under tighter control. And knowing the test result quantitatively provides information about how much to adjust the process controls. In other words, the quantitative result provides information not only about the direction of a process change, but also about the magnitude of such a process change. None of this is possible with simple, qualitative testing procedures.

EXAMPLE

Figure 6:
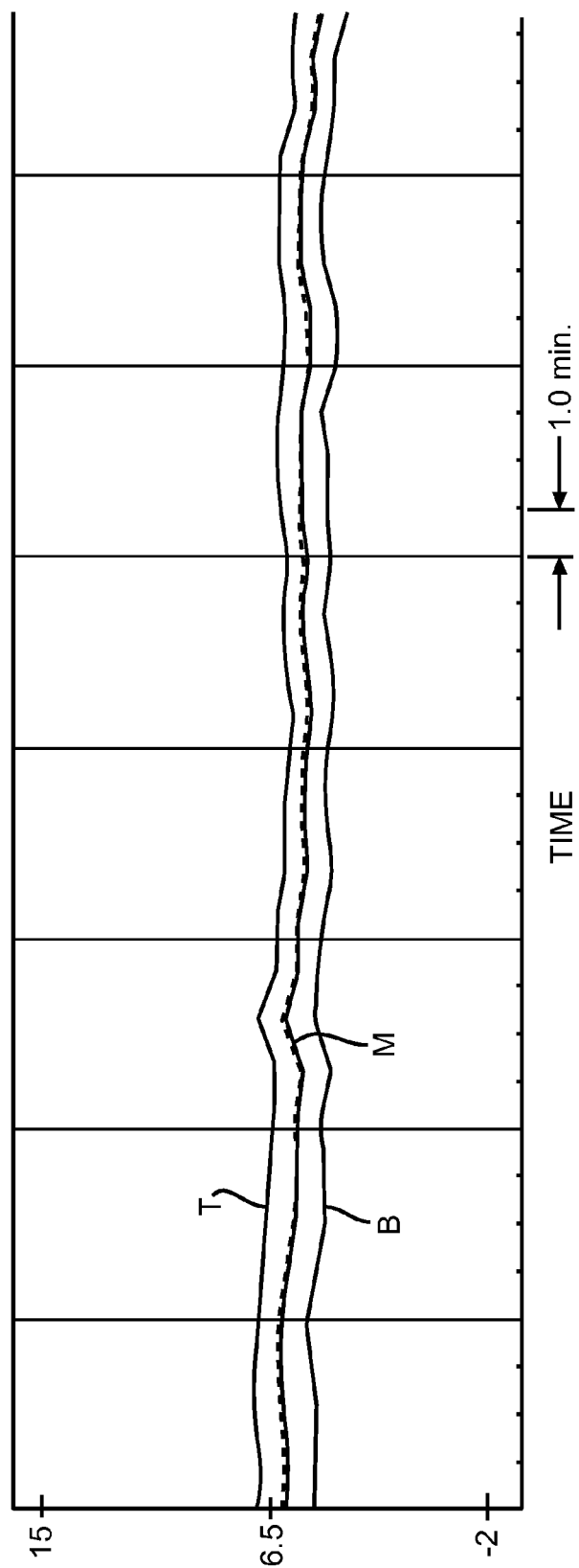
FIG. 6 is a graph of a color system variable, B-value over time, generated from a trial run as described in the Example.

Trials were conducted in a plant in Edmonton, where R-20 light density, pink residential insulation was being prepared. Installed over the manufacturing line were 4 Basler CCD cameras in a configuration much like FIG. 4A. Cognex supplied the cameras and the Vision Pro processing software. Trial runs were conducted and the blankets were chopped transversely to produce end faces, images of which were captures by the cameras. The processing software was programmed to identify three vertical regions, for top, middle and bottom ROIs within the blanket end face. Vision Pro calculated B-values for each ROI which were plotted versus time. FIG. 6 illustrates approximately 30 minutes of a typical B value trace for top (trace T), middle (trace M), bottom (trace B) and an overall average (dashed trace) for a blanket end face for a specific product. The horizontal axis is time, each minor increment being 1 minute, and the vertical axis is a scale for B-value from −2 to 15.

The principle and mode of operation of this invention have been explained and illustrated in its preferred embodiment. However, it must be understood that this invention may be practiced otherwise than as specifically explained and illustrated without departing from its spirit or scope.

What is claimed is:

1. A method of determining the cure status of a mineral fibrous product comprising:
   capturing a color digital image from a cut surface of a fibrous product using a color digital camera on-line without removing the fibrous product from the manufacturing line;
   analyzing at least one region of interest from said color digital image to obtain a color system variable for the region of interest; and
   assessing the degree of cure of the fibrous product on the basis the color system variable from the region of interest.

2. The method of claim 1 wherein a portion of the color digital image is captured from a surface that is an uncut exterior surface of the fibrous product.

3. The method of claim 1 wherein the cut section is transverse to a machine direction.

4. The method of claim 1 further comprising analyzing at least two distinct regions of interest from different positions in the Z direction of the cut surface.

5. The method of claim 4 further comprising analyzing at least 3 regions of interest in the Z direction.

6. The method of claim 1 further comprising analyzing at least two distinct regions of interest from different positions in the Y direction of the cut surface.

7. The method of claim 1 wherein the step of analyzing at least one region of interest comprises obtaining at least one of: (a) the A-value, (b) the B-value and (c) the L value of an LAB color system.

8. The method of claim 1 wherein the step of capturing an optical measurement is performed on a chopped end face.

9. The method of claim 1, wherein capturing the color digital image involves receiving visible light reflected off of the cut surface of the fibrous product.

10. A method of determining the cure status of a mineral fibrous product comprising:
    capturing an optical reflectance measurement from a sectioned face of a sectioned fibrous product on-line, without removing the fibrous product from the manufacturing line;

analyzing the optical reflectance measurement from at least one region of interest from the sectioned face; and assessing the degree of cure of the fibrous product on the basis the optical reflectance measurement at the region of interest.

11. The method of claim 10 further comprising analyzing the optical reflectance measurement from at least two regions of interest from the sectioned face.

12. The method of claim 11 wherein the at least two distinct regions of interest come from different positions in the Z direction of the sectioned face.

13. The method of claim 11 wherein the at least two distinct regions of interest come from different positions in the Y direction of the sectioned face.

14. The method of claim 10 wherein the optical reflectance measurement is a digital color image.

15. The method of claim 14 wherein the step of analyzing the region of interest comprises obtaining at least one color system variable of the image.

16. The method of claim 15 wherein the step of obtaining the color system variable comprises obtaining at least one; of (a) the A- value, (b) the B-value and (c) the L value of an LAB color system.

17. The method of claim 10 wherein the optical reflectance measurement is a spectrometric measurement.

18. The method of claim 10 wherein the step of capturing an optical measurement is performed on a chopped end face.

19. The method of claim 10, wherein capturing the color digital image involves receiving visible light reflected off of the cut surface of the fibrous product.

* * * * *